United States Patent [19]

Kampfer et al.

[11] Patent Number: 4,504,668

[45] Date of Patent: Mar. 12, 1985

[54] PROCESS FOR THE PREPARATION OF N-SULFOALKYL QUATERNARY SALTS OF NITROGEN HETEROCYCLICS

[75] Inventors: Helmut Kampfer, Cologne; Marie Hase, Bergisch Gladbach; Max Glass, Cologne, all of Fed. Rep. of Germany

[73] Assignee: Ggfa-Gevaert Aktiengesellschaft, Leverkusen, Fed. Rep. of Germany

[21] Appl. No.: 242,605

[22] Filed: Mar. 11, 1981

[30] Foreign Application Priority Data

Mar. 19, 1980 [DE] Fed. Rep. of Germany ....... 3010427

[51] Int. Cl.$^3$ ................. C07D 293/12; C07D 277/62; C07D 263/54; C07D 735/04
[52] U.S. Cl. .................................... 548/120; 548/127; 548/150; 548/179; 548/217; 548/325; 548/327; 548/565; 260/239 R
[58] Field of Search .................... 260/239 R; 548/120, 548/179, 325, 327, 217, 150, 565

[56] References Cited

U.S. PATENT DOCUMENTS 2,912,329  11/1959  Jones et al. ........................... 96/100
4,287,348  9/1981  Kitzing et al. ...................... 548/121

FOREIGN PATENT DOCUMENTS 2825246  12/1978  Fed. Rep. of Germany .
929080   7/1949   German Democratic Rep. .
1177482  9/1964   German Democratic Rep. .
1090626  11/1967  United Kingdom .

OTHER PUBLICATIONS

Maneche, Chem. Berichte, 85, pp. 160–163, (1952).

*Primary Examiner*—Glennon H. Hollrah
*Assistant Examiner*—David B. Springer
*Attorney, Agent, or Firm*—Connolly and Hutz

[57] ABSTRACT

Tertiary amines may be quaternized by heating them with a sulfoalkylating agent of this invention to a temperature of from 100° to 250° C. The sulfoalkylating agents which are believed to be hydroxy alkane sulfonic acid sulfoalkyl esters are free from sultone and are prepared by heating a hydroxy alkane sulfonic acid of propane or butane or the corresponding sultone to a temperature in the region of from 80° to 180° C. in the presence of water in an amount of 1 to 4 moles per mole of hydroxy alkane sulfonic acid or alkane sultone.

9 Claims, No Drawings

PROCESS FOR THE PREPARATION OF N-SULFOALKYL QUATERNARY SALTS OF NITROGEN HETEROCYCLICS

This invention relates to a process for the preparation of sulfoalkyl quaternary salts of tertiary amines, in particular of tertiary heterocyclic bases containing nitrogen.

These quaternary salts, which contain positively and negatively charged groups linked by covalent bonds, ar also known as betaines. They play an important part in numerous commercial processes. They are either used as such, e.g. for electroplating, or as intermediate products to be subjected to further reactions. When sulfoalkyl betaines are to be used as intermediate products, it is frequently advantageous in practice not to isolate them but to carry out the further reaction in the same reaction medium used for their preparation, in a single process step. As intermediate products, sulfoalkyl betaines play in important part in, for example, the synthesis of polymethine dyes used as spectral sensitization dyes for light-sensitive materials, in particular for photographic silver halide emulsions. This invention therefore also relates to the conversion of heterocyclic bases to polymethine dyes using the corresponding sulfoalkyl quaternary salts as intermediate products.

Methods for the preparation of sulfoalkyl quaternary bases are reacted with a sulfoalkylating agent, generally at an elevated temperature. Compounds which have been described as sulfoalkylating agents include, inter alia, halogen alkane sulfonic acids, e.g. 2-bromomethane sulfonic acid described in U.S. Pat. No. 2,503,776; sodium iodoethanesulfonate described in Belgian Pat. No. 669,308; sodium iodobutane sulfonate described in U.S. Pat. No. 2,912,329 and 3-chloro-2-hydroxypropane sulfonic acid described in German Auslegeschrift No. 1,177,482. One disadvantage of these sulfoalkylating agents is the excess of tertiary base required to bind the hydrogen halide when free sulfonic acids are used. Sultones are also known as sulfoalkylating agents, e.g. propane, butane and isopentanesultone described in German Pat. No. 929,080, propenesultone described in German Auslegeschrift No. 1,447,579 and 2-Chloropropanesultone described in British Pat. No. 1,090,626. One disadvantage of sultones is their in some cases damaging physiological action which makes them an environmental hazard and a safety hazard for persons dealing with them.

Sulfoalkylating agent which avoid the use of carcinogenic sultones have recently been described. Hydroxyalkanesulfonic acids and their salts have been described as quaternizing agents in German Offenlegungsschrift No. 2,825,246 and in Research Disclosure No. 16374/1977. A disadvantage of these quaternizing agents is the large quantities of water produced in the reaction, which inhibit quaternization and may lead to low yields unless removed by azeotropic distillation with suitable solvents.

O-sulfoalkylimidoesters have been described in Research Disclosure No. 18040/1979 and related O-sulfoalkyl isouronium betaines have been described in German Offenlegungsschrift No. 2,909,200. These new quaternizing agents also have many disadvantages. Their preparation from carbodiimides, acid nitriles or dialkylureas is relatively expensive, their thermal stability is limited and the high melting points of some of the compounds necessitate the use of solvents as reaction media.

It was therefore an object of the present invention to provide a process for the preparation of sulfoalkyl quaternary salts which would obviate the above-mentioned disadvantages.

A process for the preparation of sulfoalkyl quaternary salts of tertiary amines has now been found which is characterized by the reaction of the tertiary amine with a sulfoalkylating agent described hereinafter which is believed to be the intermolecular ester of a hydroxalkane sulfonic acid or "dimeric hydroxyalkane sulfonic acid corresponding to the general formula I

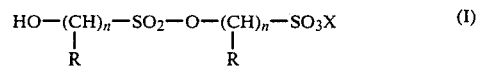

in which
R represents hydrogen or alkyl having 1 to 4 carbon atoms, in particular methyl, in which the alkyl group may be substituted, e.g. with halogen such as fluorine or chlorine;
X represents hydrogen or a cation, preferably an alkali metal cation or ammonium ion, and
n=3 or 4, preferably 3.

Particularly suitable compounds are those corresponding to formula II:

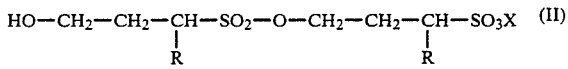

in which R and X have the meanings indicated above.

The sulfoalkylating agents of presumable structures I and II can be prepared by heating the corresponding hydroxyalkane sulfonic acid of propane or butane or the corresponding alkane sultone, having 5 or 6 ring members, preferably a 1,3-propane sultone, to a temperature in the region of from 80° to 180° C. and preferably from 120° to 150° C. in the presence of water in an amount of from 1 to 4 moles per mole of hydroxy alkane sulfonic acid or alkane sultone. The method of preparation is described in copending German Patent Application No. P 30 04 692.5 and corresponding U.S. patent application Ser. No. 230,321 filed Feb. 2, 1981 which is incorporated herein by reference.

The reaction between the sulfoalkylating agent of the present invention and the tertiary amine to be sulfoalkylated is carried out at an elevated temperature, e.g. within the range of from 80° to 250° C., preferably from 140° to 200° C.

The reaction generally proceeds smoothly within the last mentioned temperature range although it may also be carried out outside this range, depending on the nature of the solvent used.

Suitable tertiary amines include, in particular all those derivatives of ammonia ($NH_3$) in which each of the three hydrogen atoms is substituted, e.g. by a carbon atom of an alkyl or aryl group or by a carbon atom or hetero atom of a heterocyclic ring, and in particular the nitrogen atom of the tertiary amine may form part of the heterocyclic ring. Particularly suitable heterocyclic bases are therefore those corresponding to the general formula III

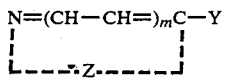

in which Z represents the atoms required to complete a heterocyclic group comprising at least one 5-membered or 6-membered heterocyclic ring; the hetero ring may have condensed to it benzene or naphthalene or also heterocyclic rings, which may be further substituted; the heterocyclic groups known from the cyanine dyes series may be suitable; e.g. pyrroline (e.g. 4,4-dimethylpyrroline); oxazoline (e.g. 4,4-dimethyloxazoline); thiazoline (e.g. 5-methyl-thiazoline); selenazoline; indoline (e.g. 3,3-dimethylindoline, 3,3-dimethyl-5-methoxyindoline and 3,3-dimethyl-5-diethylaminoindoline); benzimidazole (e.g. 1-ethyl-5-trifluoromethylbenzimidazole, 1-methyl-5-chlorobenzimidazole, 1-ethyl-5,6-dichlorobenzimidazole, 1-ethyl-5-cyanobenzimidazole, 1-methyl-5-carbethoxybenzimidazole, 1-ethyl-5-acetylbenzimidazole, 1-methylbenzimidazole-5-sulfonic acid pyrrolidide, 1-ethyl-benzimidazole-5-sulfonic acid dimethylamide, 1-ethyl-5-phenylthiobenzimidazole, 1-methyl-5-methylthiobenzimidazole and 1-methyl-5-chloro-6-methylthiobenzimidazole); oxazole (e.g. 4-methyloxazole, 4,5-diphenyloxazole, 4-methyl-5-carbethoxyoxazole, benzoxazole, 5-chlorobenzoxazole, 5-phenylbenzoxazole, 6-methoxybenzoxazole, 5-methoxybenzoxazole, 5-methyl-6-methoxybenzoxazole, 5-bromobenzoxazole, 5-iodobenzoxazole, naphtho[2,1-d]oxazole, naphtho[1,2-d]oxazole, naphtho[2,3-d]oxazole, 4,5,6,7-tetrahydrobenzoxazole and benzofuro[2,3-f]benzoxazole); thiazole, (e.g. 4-methylthiazole, 4-phenylthiazole, 4-methylthiazole-5-acrylic acid ethyl ester, benzothiazole, 5-methylbenzothiazole, 6-methylbenzothiazole, 5-chlorobenzothiazole, 5-methoxybenzothiazole, 6-methoxybenzothiazole, 5,6-dimethylbenzothiazole, 5,6-dimethoxybenzothiazole, 5-methyl-6-methoxybenzothiazole, 5-bromobenzothiazole, 5-phenylbenzothiazole, 6-methylthiobenzothiazole, 6-dimethylaminobenzothiazole, 5-chloro-6-methoxybenzothiazole, 5,6-methylene-dihydroxybenzothiazole, 6-β-cyanoethoxybenzothiazole, 5-carbomethoxy benzothiazole, 5-nitrobenzothiazole, 5-phenylthiobenzothiazole, 5-thienylbenzothiazole, 6-hydroxybenzothiazole, 4,5,6,7-tetrahydrobenzothiazole, 4-oxo-4,5,6,7-tetrahydrobenzothiazole, naphtho[2,1-d]thiazole, naphtho[1,2-d]thiazole, 4,5-dihydronaphtho[1,2-d]-thiazole, 5-methoxynaphtho[1,2-d]-thiazole, and 5,7,8-trimethoxynaphtho[1,2-d]thiazole); selenazole (e.g. benzoselenazole, 5-methylbenzoselenazole, 5,6-dimethylbenzoselenazole, 5-methoxy-benzoselenazole, 5-methyl-6-methoxybenzoselenazole, 5,6-dimethoxybenzoselenazole, 5,6-methylene-dihydroxybenzoselenazole, 6-methylbenzoselenazole, and naphtho[1,2-d]-selenazole); 1,3,4-oxadiazole (e.g. 5-methyl-1,3,4-oxadiazole and 5-phenyl-1,3,4-oxadiazole); 1,3,4-thiadiazole (e.g. 5-methyl-1,3,4-thiadiazole, 2,5-bismethylthio-1,3,4-thiadiazole, 5-benzylthio-1,3,4-thiazole, 2-mercapto-5-methylthio-1,3,4-thiadiazole; and 5-carbethoxymethylthio-1,3,4-thiadiazole); pyridine (e.g. 2-methylpyridine and 4-methylpyridine); pyrimidine (e.g. 2-methyl-4-methylthiopyrimidine); quinoline (e.g. 6-methylquinoline, 6-methoxyquinoline, 8-chloroquinoline, 6-floroquinoline, 5,6-benzoquinoline and 6,7-benzoquinoline) and imidazo[4,5-b]quinoxaline; m=0 or 1;

Y represents hydrogen, halogen, a saturated or unsaturated aliphatic group in particular one having up to 6 carbon atoms, which may be substituted, e.g. methyl, ethyl, allyl, cyanoalkyl, haloalkyl or alkoxyalkyl, or an alkoxy, e.g. carboxyalkoxy, alkylthio, e.g. carboxyalkylthio, sulfoalkylthio or carbalkoxyalkylthio, or mercapto group, Y may also represent, for example, a methine chain having 1, 3, or 5 methine groups, at the end of which is situated a N-alkylated heterocyclic base, in most cases attached at the 2-position, as known from the chemistry of cyanine dyes. Reference may be made in this connection to F. M. Hamer, "The Cyanine Dyes and Related Compounds", (1964), Interscience Publishers John Wiley & Sons. Compounds of Formula II in which Y is defined as above are known as "dequaternized cyanine dyes". When such dequaternized cyanine dyes are reacted by the process according to the invention, the products obtained may be used as sensitizing dyes without any further reaction.

The reactions are generally carried out without solvents although they may be carried out in the presence of suitable solvents. Any solvents which are inert in the reaction according to the invention and have a high dissolving power for the reactants are suitable, e.g. a phenol such as phenol or m-cresol; m-xylene, chlorobenzene and anisole.

The reactions according to the invention may be accompanied by the splitting off of water. The esters according to the invention are in most cases reacted with the bases in a molar ratio of 1:2, and 0.5 mol of water is formed per mol of base, although the reaction may also be carried out with different molar ratios, e.g. 1:1. The water of reaction is advantageously removed from the reaction vessel, for example by (1) operating under vacuum,
(2) introducing an anhydrous inert gas, e.g. nitrogen,
(3) the presence of a hehydrating agent, either in the reaction vessel (e.g. anhydride of an organic acid or $P_4O_{10}$) or in a receiver connected to the reaction vessel (e.g. $P_4O_{10}$, concentrated sulfuric acid, NaOH or some other dehydrating agent), or
(4) evaporation and freezing in a freezing apparatus.

Sulfobetaines of tertiary amines prepared by the process according to the invention include in particular those corresponding to the following formula III

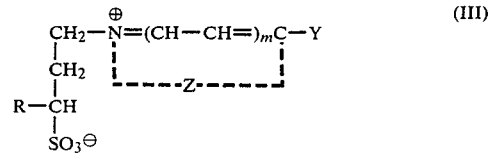

in which Y, Z, R and m have the meanings already indicated.

These compounds are used for various purposes. For example, they may be used as conducting salts in electroplating. With shitable of Y, i.e. when Y, as already mentioned above, is a methine chain having 1, 3 or 5 methine groups with a N-alkylated heterocyclic base at the end of the chain, these compounds also constitute the end products of a cyanine dye synthesis. They may be used directly for the spectral sensitization of light-sensitive silver halide emulsions. The compounds prepared by the process according to the invention are also important as intermediate products in the synthesis of polymethine dyes. For example, sulfopropyl quaternary salts of heterocyclic bases obtained by the process according to the invention are preferably not isolated but are converted in known manner to polymethine dyes after completion of the quaternization reaction without first being purified.

The process according to the invention and its variations are described in more detail in the following Examples.

EXAMPLE 1

Anhydro-1,2-dimethyl-3-[3-sulfopropyl]-5,6-dichlorobenzimidazolium hydroxide, M.p. 340° C. 21.5 g of 1,2-dimethyl-5,6-dichlorobenzimidazole and 14 g of 3-hydroxypropane sulfonic acid-(3-sulfopropyl)-ester (hereinafter referred to as "Ester 1") are dissolved in 40 ml of N-methylpyrrolidone and heated on an oil bath at a temperature of 190° C. for 8 hours under a slow stream of nitrogen. After cooling, the reaction product is triturated with 60 ml of ethanol and suction filtered.

Yield: 25.6 g=76% of the theoretical yield.

"Ester 1" has been prepared as follows:

1 mol of 1,3-propane sultone is heated under reflux with 3 mol of water at 137° C. for 2 hours. The reaction product is then freed from excess water on a rotary evaporator under a vacuum of 0.3 mm at 40° C. The ester is obtained as a viscous oil which crystallizes when left to stand and still contains 9% of water after titration. According to the $^{13}$-C NMR spectrum, this product is free from 1,3-propane sultone.

"Ester 1" is characterized by NMR spectroscopic data; it is found to have the following $^{13}$C shifts (ppm, relative to TMS=O, in D$_2$O in the presence of dioxane):

25.2; 27.8; 48.8; 61.1 and 69.5.

EXAMPLE 2

Anhydro-1,2-dimethyl-5-cyano-3-(3-sulfopropyl)benzimidazolium hydroxide, M.p. 345° C.

23 g of 1,2-dimethyl-5-cyanobenzimidazole and 16.3 g of the Ester 1 are heated to 175° C. as described in Example 1. The product is worked up with 45 ml of methanol.

Yield: 26.4 g=69.2%.

EXAMPLE 3

Anhydro-1,2-dimethyl-5-pyrrolidinosulfonyl-3-(3-sulfopropyl)-benzimidazolium hydroxide, M.p. 327° C. (decomposition).

Prepared from 16.8 g of 1,2-dimethyl-5-pyrrolidinosulfonyl-benzimidazole and 10.9 g of Ester 1 by heating for 4 hours at 185° C. by the method described in Example 1 but without solvent. The product is worked up with ethanol.

Yield: 17.5 g=73%.

EXAMPLE 4

Anhydro-2-methyl-3-(3-sulfopropyl)-naphtho[1,2-d]-oxazolium hydroxide, M.p. 273°–274° C.

18.3 g of 2-methylnaphtho[1,2-d]-oxazole, 14.2 g of Ester 1 and 7 g of phenol are heated in an oil bath at 180° C. under nitrogen for 6 hours. The product is worked up with 30 ml of ethanol.

Yield: 18.5 g=61%.

EXAMPLE 5

Anhydro-2-methyl-3-(3-sulfopropyl)-benzothiazolium hydroxide. m.p. 290° C.

7.5 g of 2-methylbenzothiazole and 6.6 g of Ester 1 are heated to 175° C. for 5 hours under a stream of nitrogen. After cooling, the reaction product is worked up with 20 ml of ethanol.

Yield: 9.3 g=68%.

EXAMPLE 6

Anhydro-2-methyl-5-chloro-3-(3-sulfopropyl)-benzothiazolium hydroxide, m.p. 288°–290° C.

(a) 184 g of 2-methyl-5-chlorobenzothiazole and 140 g of Ester 1 are heated to 175°–180° C. for 1.5 hours. 20 g of phenol dissolved in 20 ml of toluene are then added and the reaction mixture is heated for a further 4 hours in a stream of nitrogen. After cooling, the product is worked up with 80 ml of ethanol.

Yield: 276 g=90%.

(b) The same yield is obtained when the reactants are heated to 175° C. for 5 hours without the use of phenol and toluene.

EXAMPLE 7

Anhydro-2-methyl-3-(3-sulfobutyl)-benzothiazolium hydroxide, m.p. 246° C.

From 6 g of 2-methylbenzothiazole and 5.9 g of 4-hydroxybutane-2-sulfonic acid-(3-sulfobutyl)-ester ("Ester 2") by 3.5 hours heating at 175° C. and working up with isopropanol and then acetone.

"Ester 2" has been prepared as follows:

4-hydroxy butane-2-sulfonic acid having a water content of 14.7% is heated on an oil bath temperature of 170° C. for 2 hours, the reaction mixture having a temperature of 144°–146° C. The water split off in the reaction is then evaporated off under a vacuum of 0.5 and a temperature of 40° C., using a receiver cooled to −38° C. The yield determined by the $^{13}$C NMR spectrum was 96.6%.

"Ester 2" was characterized by NMR spectroscopy and was found to have the following $^{13}$C shifts: 15.4; 31.7; 34.4; 53.6; 60.0 and 68.5.

EXAMPLE 8

Anhydro-2-methyl-3-(sulfopropyl)-naphtho-[1,2-d]thiazolium hydroxide, m.p. 277° C.

(a) 8 g of Ester 1 and 5 ml of acetic acid anhydride are heated to 140° C. for 2 hours, and then to 175° C. for a further 4 hours after the addition of 10 g of 2-methylnaphthol[1,2-s]-thiazole.

Yield of 7.1 g=44% of the compound is obtained after working up with ethanol.

(b) 50 g of Ester 1 are heated to 140° C. for 4 hours in a rotary evaporator under a vacuum of 20 mm Hg while cooling liquid is pumped through the condenser at −20° C. 50 g of 2-methylnaphtho[1,2-d]-thiazole are then added and the reaction mixture is heated to 175° C. for a further 4 hours. The reaction product is recrystallized from m-cresol/ethanol.

Yield: 75 g=93%.

EXAMPLE 9

3-Ethyl-5-[3-sulfopropyl)-2-benzothiazolylidene]rhodanine, sodium salt, m.p. 340° C.

6.2 g of 3-(benzothiazol-2-ylthio)-propanesulfonic acid sodium, 3 g of Ester 1 and 2 g of phenol are heated to 175° C. for 8.5 hours under nitrogen. The reaction product is taken up in ethanol, 3 g of 3-ethylrhodanine and 2 g of triethylamine are added, and the reaction mixture is stirred for 3 hours. The dye is recrystallized from methanol/water.

Yield: 2.6 g=25%, absorption maximum: 427 nm.

EXAMPLE 10

Anhydro-2-methyl-3-(3-sulfopropyl)-5-methoxybenzoselenazolium hydroxide, m.p. 299°–302° C.

By heating 6.8 g of 2-methyl-5-methoxybenzoselenazole, 3.9 g of Ester 1, 2 ml of acetic acid anhydride and 2 ml of m-cresol to 175° C. for 7.5 hours in the course of which a slow stream of nitrogen is passed through for ½ hour, and working up the product with ethanol.

Yield: 6.8 g=65%.

EXAMPLE 11

Anhydro-2-methyl-3-(3-sulfopropyl)-5-methyl-6-methoxybenzoselenazolium hydroxide, m.p. 298°–299° C. From 7.2 g 2,5-dimethyl-6-methoxybenzoselenazole, 4 g of Ester 1 and 3 g of phenol by the method described in Example 10 in 8 hours at 175° C.

Yield: 7.7 g=71%.

EXAMPLE 12

Anhydro-2-methyl-3-(3-sulfopropyl)-5-phenylbenzoxazolium hydroxide, m.p. 288°–290° C.

16.7 g of 2-methyl-5-phenylbenzoxazole and 5 g of phosphorus pentoxide are added to 11.2 g of Ester 1 and the mixture is heated gently, to 30°–40° C. The temperature then rises spontaneously to 90° C. The mixture is then heated for a further 30 minutes to 175° C. (oil bath temperature) with rapid stirring; crystallization sets in. The product is cooled and mechanically broken down and then stirred up with 20 ml of methanol, suction filtered and washed with a small quantity of cold methanol.

Yield: 17.3 g=65%.

EXAMPLE 13

3-Ethyl-5-[5methylthio-3-(3-sulfopropyl)-1,3,4-thiadiazol-2-ylidene]-rhodanine, pyridine salt, m.p. 203°–204° C.

1.8 g of 2.5-bis-methylthio-1,3,4-thiadiazole and 2.8 g of Ester 1 are heated to 140° C. with stirring for 2 hours with the addition of 0.5 g of phenol. The reaction mixture is cooled to 80° C. 1.6 g of 3-ethylrhodanine and 5 ml of pyridine are added and the reaction mixture is maintained at 80° C. for 5 minutes. The dye is left to crystalline for 2 hours, suction filtered and recrystallized from 10 ml of n-propanol.

Yield: 1.2 g=24.4%. Absorption maximum: 420 nm.

EXAMPLE 14

3,3'-Bis-[3-sulfopropyl]-4,5; 4',5'-dibenzothiacyanine, triethylamine salt, m.p. 291° C.

22 g of 2-mercaptonaphtho[1,2-d]-thiazole, 30 g of Ester 1 and 5 g of phenol are melted at 175° C. and stirred at 175° C. for 6 hours under a stream of nitrogen. After cooling to 100° C., the reaction product is dissolved in 60 g of phenol, and a melt of 32 g of anhydro-2-methyl-3-(3-sulfopropyl)-naphtho[1,2-d]-thiazolium hydroxide in 60 g of phenol is added. When the reaction mixture has cooled to 50°–60° C., 34 ml of triethylamine are added dropwise with stirring. The reaction mixture is left to react for a further 10 minutes and 300 ml of acetonitrile heated to 50° C. are added. The reaction mixture is left to stand for 4 hours and the dye which has separated by that time is suction filtered and recrystallized from methylene chloride/methanol.

Yield: 15 g, absorption maximum: 455 nm.

We claim:

1. In a process for the preparation of sulfoalkyl quaternary salts of tertiary amines by reacting a tertiary amine corresponding to the formula

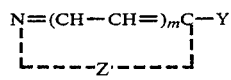

in which
Y represents hydrogen, halogen, a saturated or unsaturated aliphatic group having up to 6 carbon atoms, an alkoxy or alkylthio group, or mercapto;
Z represents the atoms required to complete a heterocyclic group comprising at least one 5-membered or 6-membered heterocyclic ring; and
m is 0 or 1;
with a sulfoalkylating agent at a temperature of from 100° to 250° C., the improvement which comprises reacting said tertiary amine with the sulfoalkylating agent which is a dimer that is obtained by heating a hydroxy alkane sulfonic acid of propane or butane or the corresponding alkane sultone having 5 or 6 ring members to a temperature in the region of from 80° to 180° C. in the presence of water in an amount of from 1 to 4 moles per mole of hydroxy alkane sulfonic acid or alkane sultone.

2. Process as claimed in claim 1 wherein the reaction is carried out at a temperature of from 140° to 200° C.

3. Process as claimed in claim 1, wherein the reaction is carried out in the presence of a solvent.

4. A process as claimed in claim 1, wherein the reaction of the tertiary amine with the sulfoalkylating agent is carried out in the presence of a phenol solvent which is inert to the reaction.

5. A process as claimed in claim 1, wherein the reaction of the tertiary amine with the sulfoalkylating agent is carried out in the presence of an anhydride of an organic acid dehydrating agent.

6. A process as claimed in claim 1, wherein the reaction of the tertiary amine and the sulfoalkylating agent is carried out in the presence of phosphorus pentoxide.

7. A process as claimed in claim 1, wherein the product of the reaction of the tertiary amine and the sulfoalkylating agent, without isolation is converted to a cyanine dye.

8. In the process for the preparation of sulfoalkyl quaternary salts of tertiary amines by reacting a tertiary amine corresponding to the formula

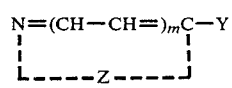

in which
Y represents hydrogen, halogen, a saturated or unsaturated aliphatic group having up to 6 carbon atoms, an alkoxy or alkylthio group, or mercapto;
Z represents the atoms required to complete a heterocyclic group comprising at least one 5-membered or 6-membered heterocyclic ring; and
m is 0 or 1;
with a sulfoalkylating agent at a temperature of from 100° to 250° C., the improvement which comprises reacting said tertiary amine with the sulfoalkylating agent which is obtained by heating 3-hydroxy propane sulfonic acid or 1,3-propane sultone to a temperature in the region of from 80° to 180° C. in the presence of water in an amount of from 1 to 4 moles per mole of 3-hydroxy propane sulfonic acid or 1,3-propane sultone, and being characterized by the following $^{13}$C-NMR-shifts (ppm, relative to TMS=0, in D$_2$O in the presence of dioxane): 25.2; 27.8; 48.8; 61.1 and 69.5.

9. In a process for the preparation of sulfoalkyl quaternary salts of tertiary amines by reacting a tertiary amine corresponding to the formula

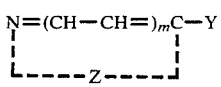

in which

Y represents hydrogen, halogen, a saturated or unsaturated aliphatic group having up to 6 carbon atoms, an alkoxy or alkylthio group, or mercapto;

Z represents the atoms required to complete a heterocyclic group comprising at least one 5-membered or 6-membered heterocyclic ring; and m is 0 or 1;

with a sulfoalkylating agent at a temperature of from 100° to 250° C., the improvement which comprises reacting said tertiary amine with the sulfoalkylating agent which is obtained by heating 4-hydroxy butane-2-sulfonic acid or 3-methyl-1,3-propane sultone to a temperature of from 80° to 180° C. in the presence of water in an amount of from 1 to 4 moles per mole of 4-hydroxy butane-2-sulfonic acid or 3-methyl-1,3-propane sultone, and being characterized by the following $^{13}$C-NMR-shifts (ppm, relative to TMS=0, in the presence of dioxane); 15.4; 31.7; 34.4; 53.6; 60.0 and 68.5.

* * * * *